United States Patent [19]

Plöger et al.

[11] 3,984,543
[45] Oct. 5, 1976

[54] THERAPEUTIC METHODS EMPLOYING CYCLIC AMINOPHOSPHONIC ACIDS

[75] Inventors: Walter Plöger, Hilden Rhineland; Manfred Schmidt-Dunker, Dusseldorf; Christian Gloxhuber, Haan Rhineland, all of Germany

[73] Assignee: Henkel & Cie GmbH, Dusseldorf-Holthausen, Germany

[22] Filed: Aug. 1, 1975

[21] Appl. No.: 601,040

Related U.S. Application Data

[62] Division of Ser. No. 498,996, Aug. 20, 1974, Pat. No. 3,925,456.

[30] Foreign Application Priority Data

Aug. 27, 1973   Germany............................ 2343195

[52] U.S. Cl................................. 424/204; 424/49; 424/54
[51] Int. Cl.² ................. A61K 31/675; A61K 7/16; A61K 7/22
[58] Field of Search ..................................... 424/204

[56] References Cited

UNITED STATES PATENTS 3,678,164   7/1972   Francis .............................. 424/204
3,719,756   3/1973   Francis .............................. 424/204

OTHER PUBLICATIONS

Russell et al., Calc. Tiss. Res. 6, pp. 183–196 (1970) by Springer–Verlag 1970.

Fleisch et al., Science, vol. 165, pp. 1262–1264 (reprinted), 1969, by the Amer. Assoc. for the Advancement of Sci.

Primary Examiner—Donald B. Moyer
Attorney, Agent, or Firm—Hammond & Littell

[57] ABSTRACT

Therapeutic methods employing cyclic aminophosphonic acids having the formula

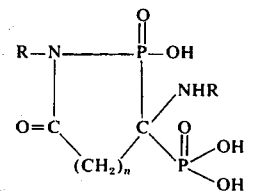

wherein R is a member selected from the group consisting of hydrogen and alkyl having from 1 to 6 carbon atoms and n is an integer from 1 to 4; as well as their water-soluble salts. The cyclic aminophosphonic acids are excellent sequestering agents especially for alkaline earth metal ions, useful in cosmetic preparations such as toothpastes and mouthwashes where they prevent formation of tartar and plaque and in therapy in the treatment of diseases related to the abnormal deposition or dissolution of difficulty soluble calcium salts in the animal body.

9 Claims, No Drawings 3,984,543

THERAPEUTIC METHODS EMPLOYING CYCLIC AMINOPHOSPHONIC ACIDS

This is a division of Ser. No. 498,996, filed Aug. 20, 1974, now U.S. Pat. No. 3,925,456.

THE PRIOR ART

It is known that monocarboxylic acid amides or nitriles can be reacted with phosphorus trihalides or with phosphorus trihalides and phosphorous acid to give 1-aminoalkane-1,1-diphosphonic acids. Similar reactions with short-chained dicarboxylic acid diamides or dinitriles have not previously been reported.

OBJECTS OF THE INVENTION

An object of the present invention is the development of a cyclic aminophosphonic acid derivative selected from the group consisting of (1) compounds of the formula

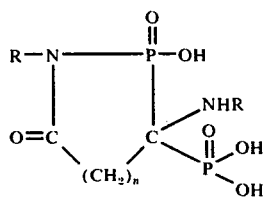

wherein R is a member selected from the group consisting of hydrogen and alkyl having from 1 to 6 carbon atoms and $n$ is an integer from 1 to 4, and (2) water-soluble salts thereof.

Another object of the present invention is the development of a process for the production of the above cyclic aminophosphonic acids or their water-soluble salts.

Another object of the present invention is the development of a process for the delaying or inhibiting of the precipitation of alkaline earth metal ions from solution by the use of stoichiometric to sub-stoichiometric amounts of the above cyclic aminophosphonic acids or their water-soluble salts.

A further object of the present invention is the development of a method for delaying the setting time for gypsum which comprises adding to the mixture of plaster materials and water a small amount of the above cyclic aminophosphonic acids or their water-soluble salts.

A yet further object of the present invention is the development of a method for the treatment of diseases related to the abnormal deposition or dissolution of difficulty soluble calcium salts which comprises administering a safe but effective amount of at least one of the above cyclic aminophosphonic acids or their water-soluble salts to the warm-blooded animal.

These and other objects of the invention will become more apparent as the description thereof proceeds.

DESCRIPTION OF THE INVENTION

The above objects have been achieved by the development of new cyclic aminophosphonic acid derivative selected from the group consisting of (1) compounds of the formula

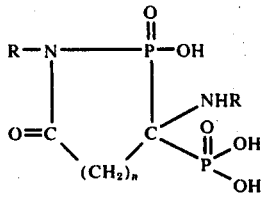

wherein R is a member selected from the group consisting of hydrogen and alkyl having from 1 to 6 carbon atoms and $n$ is an integer from 1 to 4, and (2) water-soluble salts thereof.

It has now been found that reactions of short-chained dicarboxylic acid diamides or dinitriles with phosphorus trihalides or with phosphorus trihalides and phosphorous acid do not yield tetraphosphonic acids in a similar manner as the corresponding reactions with monocarboxylic acid amides or nitriles give 1-aminoalkane-1,1-diphosphonic acids. Rather it was surprisingly noted that by reacting dicarboxylic acid derivatives of the formula $$X - (CH_2)_n - X$$

wherein $n$ is an integer from 1 to 4 and X represents the radicals —CN, —CONH$_2$ or —CONHR' wherein R' is an alkyl having 1 to 6 carbon atoms, with phosphorus trihalides or phosphorus trihalides and phosphorous acid, with subsequent acid hydrolysis, the new cyclic aminophosphonic acids of Formula I are obtained.

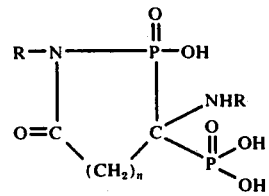

I wherein R is hydrogen or alkyl of 1 to 6 carbon atoms and $n$ is an integer of 1 to 4, or their water-soluble salts. The compounds of Formula I are readily transformed into their water-soluble salts.

More particularly, the process of the present invention for the production of the cyclic aminophosphonic acids of Formula I consists essentially of the steps of reacting a diacid compound of the formula $$X - (CH_2)_n - X$$

wherein $n$ is an integer from 1 to 4 and X is a member selected from the group consisting of —CN, —CONH$_2$ and —CONHR', where R' is alkyl having 1 to 6 carbon atoms, with at least the stoichiometric amount of a phosphorus reactant selected from the group consisting of a phosphorus trihalide and a mixture of a phosphorus trihalide and phosphorous acid, subjecting the resulting reaction product to an acid hydrolysis by the action of an aqueous media selected from the group consisting of water and an aqueous mineral acid solution, and recovering said cyclic aminophosphonic acid derivative.

The above reaction can be so carried out, for example, that a dicarboxylic acid diamide is first melted with phosphorous acid, and that PCl$_3$ is slowly added under stirring. The reaction product obtained, which is mostly viscous, is subsequently hydrolyzed by the addition of water. The addition of acids, such as mineral acids, is not necessary, because the reaction product itself is acid reacting.

However, when starting from dicarboxylic acid dinitrile, the latter can be dissolved in an inert solvent, such as dioxane or chlorinated hydrocarbons, and subsequently mixed with phosphorus trihalide. Then phosphorous acid is added and, with the addition of water, the reaction product is hydrolyzed. In the last mentioned method, the phosphorous acid can also be omitted, if desired.

In the above reactions, the phosphorus trihalides which can be used are particularly phosphorus trichloride and phosphorus tribromide. The latter was found to be particularly suitable, if the nitriles are employed as the starting material.

The molar quantitative ratio of the dicarboxylic acid derivative to the phosphorus reactant is 1:2 to 1:6, preferably 1:4. The dicarboxylic acid amides can also include those where one hydrogen atom is substituted in the amino groups by an alkyl radical with 1 to 6, preferably 1 to 4 carbon atoms.

Preferably, the above-mentioned dicarboxylic acid derivatives of malonic acid, succinic acid and glutaric acid are used.

The new cyclic aminophosphonic acids are frequently obtained as monohydrates and can be transformed by drying in the vacuum oven at about 80° C into the products without water of hydration. The titrimetrically determined molecular weights do not, at first, permit any differentiation between the monohydrate of the cyclic structural Formula I above and the following aliphatic Formula II

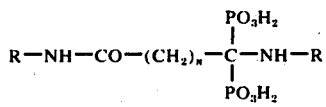

where, again, $n$ is an integer from 1 to 4 and R = hydrogen or alkyl with 1 to 6 carbon atoms. However, by determining the content of water of crystallization, it was ascertained that Formula I is correct and that compounds of Formula II are formed at best only in an insignificant amount.

The cyclic aminophosphonic acids can be easily transformed, if desired, into the water-soluble salts, for example, by partial or complete neutralization with corresponding bases. The salts correspond to the following Formula III

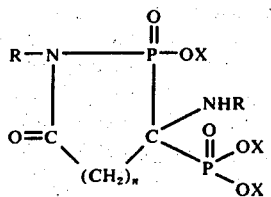

where X denotes hydrogen, $HG_4$ or a metal cation, such as an alkali metal, but where at most two hydrogen atoms are present, R = hydrogen or alkyl with 1 to 6, preferably 1 to 4 carbon atoms and n is an integer from 1 to 4.

The new cyclic aminophosphonic acids are excellent sequestering agents for polyvalent metal ions, particularly di- and tri-valent metal ions. They are particularly suitable as sequestering agents for alkaline earth metal ions, so that they can be used for many technical applications, such as in detergents and cleansers, as well as in water treatment. They can be employed in stoichiometric and substoichiometric amounts as sequestering agents for alkaline earth metal ions. They also have a stabilizing effect on percompounds.

They are also suitable as additives to delay the setting of gypsum and as ceramic slip liquifiers. For delaying the setting of gypsum, the potassium, sodium or ammonium salts, in addition to the acids, can also be used. The corresponding lithium salts as well as zinc and magnesium salts are likewise suitable.

Furthermore, they can be used in mouth washes and tooth pastes in order to avoid the information of tartar or plaque. The suitability of the cyclic aminophosphonic acids to be used according to the invention for tartar treatment and prophylaxis, results from their capacity of inhibiting the formation of crystals in the precipitation of calcium apatite already in small amounts. Calcium apatite, which is precipitated in the presence of the cyclic aminophosphonic acids, according to the invention, is X-ray amorphous, in contrast to crystalline apatite, which is usually formed without this addition.

The new cyclic aminophosphonic acids and their water-soluble alkali metal and ammonium salts are suitable as pharmacological active substances in pharmaceutical products. They have therapeutic and/or prophylactic effects in the treatment of a number of diseases, which are related to the abnormal deposition or dissolution of difficulty soluble calcium salts in the animal body. These diseases can be divided into two categories:

1. Abnormal depositions of difficultly soluble calcium salts, mostly calcium phosphate, cause bone malformations, pathological hardening of tissues and secretions in organs.

2. The abnormal dissolution of hard tissues causes losses of hard bone substance, which cannot be replaced or only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neutritis, tetany.

In addition to the free cyclic aminophosphonic acids, their pharmacologically harmless salts, such as the alkali metal salts, for example, sodium or potassium or the ammonium salts or the substituted ammonium salts, such as the lower alkanol ammonium salts like the mono-, di-, or tri-ethanol ammonoum salts can be used, for use in pharmaceutical preparations in the treatment of these diseases or for their prophylaxis. Both the partial salts, in which only a part of the acid protons are replaced by other cations, and full salts can be used, but partial salts, which react substantially neutral in aqueous solution (pH 5 to 9) are preferred. Mixtures of the above-mentioned salts can likewise be used.

The dosage range of the cyclic aminophosphonic acids can be from 0.05 to 500 mg per kg of the animal body weight. The preferred dose is 1 to 20 mg per kg of body weight, and can be administered up to four times daily. The higher doses are necessary for oral application, due to the limited resorption. Doses under 0.05 mg per kg of body weight have little effect on the pathological calcification or dissolution of bone substance. Doses above 500 mg/kg of body weight may have toxic side effects in the long run. The cyclic aminophosphonic acid derivatives can be administered orally, subcutaneously or intraperitoneally in the form of tablets, pills, capsules or as injectable solutions. For animals the cyclic aminophosphonic acid derivatives can also be used as part of the feed or of feed additives. The following specific examples are illustrative of the practice of the invention without being limitative in any manner.

EXAMPLE 1

2-Hydroxy-2-oxo-3-amino-3-phosphonyl-5-oxo-1-aza-2-phospha-cyclopentane

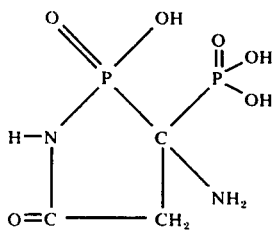

a. 102 gm of malonic acid diamide (1.0 mol) and 164 gm of $H_3PO_3$ (2.0 mols) were melted with exclusion of moisture at 70° C and mixed slowly under stirring with 175 ml of $PCl_3$ (2.0 mols). a viscous, yellow mass was formed which, after 4 hours, was hydrolyzed with 1 liter of $H_2O$. After filtration with activated carbon, the filtrate was concentrated to 400 ml. On the addition of 4 liters of ethanol thereto, a white crystalline substance was precipitated. The 2-hydroxy-2-oxo-3-amino-3-phosphonyl-5-oxo-1-aza-2-phospha-cyclopentane was dried at 50° C in a vacuum drying oven. The crude yield was 142 gm  53% of the theory.

b. 33 gm of malodinitrile (0.5 mol) was dissolved in 200 ml of dioxane and quickly mixed with 140 ml of $PBr_3$ (1.5 mols). Then a solution of 41 gm of $H_3PO_3$ (0.5 mol) in 100 ml of dioxane was added slowly thereto under stirring at 80° C. The yellow solution was stirred for another 4 hours and then hydrolyzed with 500 ml of $H_2O$. After filtering with activated carbon, the solution was concentrated, the residue was taken up in 200 ml of $H_2O$ and a white crystalline substance was precipitated therefrom with 2 liters of ethanol. Crude yield was 50 gm  38% of the theory.

The compound was isolated as a dihydrate of 2-hydroxy-2-oxo-3-amino-3-phosphonyl-5-oxo-1-aza-2-phosphacyclopentane. The titrimetrically determined molecular weight was 266 (calc. 266.1).

Analysis: Calculated: 13.54%, C; 4.54%, H; 10.53%, N; 23.28%, P. Found: 13.48%, C; 4.20%, H; 9.97%, N; 23.05%, P.

After intensive drying, the anhydrous compound was obtained with a molecular weight, as determined titrimetrically, of 228 (calc. 230).

In the IR-spectrum the compound shows a $\nu$ CO band at 1670 cm$^{-1}$ and a $\delta$ NH band at 1615 cm$^{-1}$. M.P. 180° C with decomposition.

EXAMPLE 2

2-Hydroxy-2-oxo-3-amino-3-phosphonyl-6-oxo-1-aza-2-phospha-cyclohexane

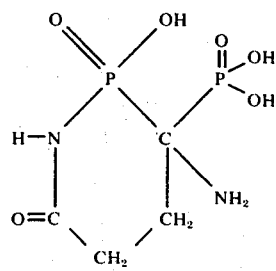

a. 232 gm of succinic acid diamide (2.0 mols) and 328 gm of $H_3PO_3$ (4.0 mols) were melted with exclusion of moisture at 70° C and mixed slowly under stirring with 350 ml of $PCl_3$ (4.0 mols). After 4 hours the resulting viscous, yellow mass was hydrolyzed with 2 liters of $H_2O$. The solution was filtered with activated carbon and concentrated to 500 ml. On the addition of 3 liters of ethanol and 3 liters of acetone, a white crystalline substance was precipitated. Yield of the crude 2-hydroxy-3-oxo-3-amino-3-phosphonyl-6-oxo-1-aza-2-phospha-cyclohexane was 180 gm $\triangleq$ 35% of the theory.

b. 40 gm of succinic acid dinitrile (0.5 mol) were dissolved in 400 ml of dioxane and 190 ml of $PBr_3$ were added slowly in drops at 70° C. After stirring for another 4 hours at 70° C, the viscous yellow mass was hydrolyzed with 200 ml of $H_2O$. After filtration with activated carbon, the dioxane was separated and a white, crystalline substance was precipitated from the aqueous phase with 1 liter of acetone. Crude yield 16 gm $\triangleq$ 12% of the theory.

The compound was obtained as a monohydrate. The titrimetrically determined molecular weight was 260 (calc. 262.1).

After drying at 80° C in the vacuum drying oven, the anhydrous cyclic compound was obtained with a molecular weight of 244 (calc. 244).

Analysis: Calculated: 19.68%, C; 4.13%, H; 11.48%, N; 25.38%, P. Found: 19.66%, C; 4.07%, H; 11.24%, N; 25.32%, P.

The IR-spectrum of the substance shows a very wide $\nu$ CO band at 1640 cm$^{-1}$ which covers the $\delta$ NH band. M.P. 320° C with decomposition.

EXAMPLE 3

1-Methyl-2-hydroxy-2-oxo-3-methylamino-3-phosphonyl-6-oxo-1-aza-2-phospha-cyclohexane

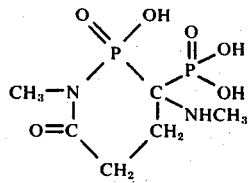

72 gm N,N'-succinic acid bismethylamide (0.5 mol) and 164 gm of $H_3PO_3$ (2.0 mols) were melted at 70° C and then 175 ml of $PCl_3$ (2.0 mols) were added slowly in drops while stirring. The mass was left for 5 hours at 70° C and then hydrolyzed with 250 ml of $H_2O$. The suspension was filtered with activated carbon and a white substance was precipitated from the filtrate with addition of 3 liters of ethanol and 1 liter of acetone. Crude yield 130 gm ≙ 90% of the theory.

On drying at 50° C, the compound was obtained as a monohydrate. Titrimetrically the molecular weight was determined at 290 (calc. 290).

Analysis: Calculated: 24.84%, C; 5.56%, N; 21.35%, P. Found: 27.74%, C; 5.56%, H; 9.62%, N; 21.40%, P.

After intensive drying the anhydrous cyclic compound 1-methyl-2-hydroxy-2-oxo-3-methylamino-3-phosphonyl-6-oxo-1-aza-2-phospha-cyclohexane was obtained with a molecular weight of 272 (calc. 272).

The compound shows in the IR-spectrum a ν CO band at 1665 cm⁻¹. M.P. 320° C with decomposition.

EXAMPLE 4

1-Ethyl-2-hydroxy-2-oxo-3-ethylamino-3-phosphonyl-6-oxo-1-aza-2-phospha-cyclohexane

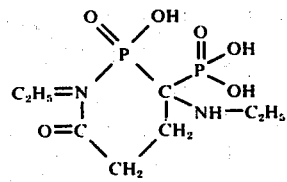

73.0 gm of N,N'-succinic acid bisethylamide (0.424 mol) and 140 gm of $H_3PO_3$ (1.7 mol) were melted in a 1 liter flask at 70° C. Then, 149 ml of $PCl_3$ (1.7 mol) were added slowly while stirring. After 5 hours at 70° C, the mass was hydrolyzed with 250 ml of $H_2O$ and the resulting suspension was filtered with activated carbon. The white phosphonic acid was precipitated from the filtrate with addition of 1 liter of ethanol and 1 liter of acetone. Crude yield 88.5 gm 69% of the theory.

After drying for 4 hours in the drying oven, the anhydrous cyclic compound 1-ethyl-2-hydroxy-2-oxo-3-ethylamino-3-phosphonyl-6-oxo-1-aza-2-phospha-cyclohexane was obtained. The titrimetric determination of the molecular weight gave 299 (calc. 300.2).

Analysis: Calculated: 32.01%, C; 6.04%, H; 9.33%, N; 20.64%, P. Found: 31.60%, C; 6.20%, H; 9.21%, N; 20.4%, P.

The IR-spectrum of the compound shows a strong ν CO band at 1605 cm⁻¹. M.P. 240° C with decomposition (sinters above 205° C).

EXAMPLE 5

1-Butyl-2-hydroxy-2-oxo-3-butylamino-3-phosphonyl-6-oxo-1-aza-2-phospha-cyclohexane

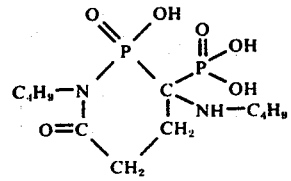

91.3 gm of N,N'-succinic acid bisbutylamide (0.4 mol) and 131 gm of $H_3PO_3$ (1.6 mol) were melted at 70° C and then 140.2 ml of $PCl_3$ (1.6 mol) were added slowly in drops. A viscous yellow mass is formed which is hydrolyzed, after another 6 hours at 70° C with 300 ml of $H_2O$. After filtering the hot solution with activated carbon, the white phosphonic acid 1-butyl-2-hydroxy-2-oxo-3-butylamino-3-phosphonyl-6-oxo-1-aza-2-phospha-cyclohexane was precipitated from the filtrate with ethanol and acetone. Yield 47 gm ≙ 31% of the theory.

After drying at 50° C, the compound was obtained as a monohydrate. The molecular weight was determined by titration at 377 (calc. 374).

Analysis: Calculated: 38.50%, C; 7.54%, H; 7.48%, N; 16.55%, P. Found: 38.31%, C; 7.37%, H; 6.63%, N; 15.91%, P.

After drying at 80°C in the vacuum drying oven, the anhydrous compound was obtained. The molecular weight was determined at 355 (calc. 356).

In the IR-spectrum, the substance showed a ν CO band at 1605 cm⁻¹.

EXAMPLE 6

2-Hydroxy-2-oxo-3-amino-3-phosphonyl-7-oxo-1-aza-2-phospha-cycloheptane

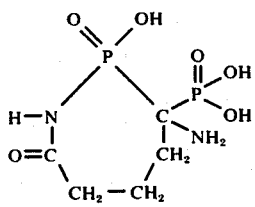

a. 55 gm of glutaric acid diamine (0.42 mol) and 140 gm of $H_3PO_3$ (1.7 mol) were melted at 70° C and then mixed slowly with 149 ml of $PCl_3$ (1.7 mol). After another 4 hours at 80° C, the mass was hydrolyzed with 400 ml of $H_2O$ and the hot solution was filtered with activated carbon. The white diphosphonic acid was precipitated from the filtrate with ethanol and acetone. Crude yield 40 gm ≙ 35% of the theory.

b. 94 gm of glutaric acid dinitrile (1.0 mol) were dissolved in 200 ml of dioxane and 278 ml of $PBr_3$ (3.0 mols) were added slowly in drops at 35° C. Subsequently the mixture was heated to 70° C and mixed slowly with a solution of 82 gm of $H_3PO_3$ (1.0 mol) in 200 ml dioxane. After 16 hours at 70° C the mass was hydrolyzed with 250 ml of $H_2O$. The mass was then filtered with activated carbon and the aqueous phase was separated from the filtrate. The white phosphonic acid was precipitated with ethanol and acetone. Crude yield 55 gm ≙ 20% of the theory.

After brief drying at 50° C, the compound 2-hydroxy-2-oxo-3-amino-3-phosphonyl-7-oxo-1-aza-2-phospha-cycloheptane was obtained as a monohydrate. The molecular weight was determined by titrimetry as 276 (calc. 276).

Analysis: Calculated: 21.75%, C; 5.11%, H; 10.15%, N; 22.43%, P. Found: 21.67%, C; 4.87%, H; 9.45%, N; 22.7%, P.

In the IR-spectrum of the substance, the ν CO band was 1660 cm⁻¹ and the δ NH band at 1615 cm⁻¹. After drying at 80° C in the vacuum oven, the anhydrous substance was obtained with a molecular weight of 260 (calc. 258). M.P. 285° C with decomposition.

EXAMPLE 7

1-Methyl-2-hydroxy-2-oxo-3-methylamino-3-phosphonyl-7-oxo-1-aza-2-phospha-cycloheptane

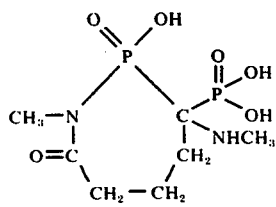

63.2 gm of N,N'-glutaric acid bismethylamide (0.4 mol) and 131 gm of $H_3PO_3$ (1.6 mol) were melted at 70° C and 140 ml of $PCl_3$ (1.6 mol) were slowly added in drops. The resulting viscous yellow mass was held for another 6 hours at 70° C and then hydrolyzed with 250 ml of $H_2O$. The solution was then boiled with activated carbon and filtered. After cooling, the white phosphonic acid was precipitated with ethanol and acetone. Crude yield 57.5 gm ≙ 47% of the theory.

After drying at 50° C, the 1-methyl-2-hydroxy-2-oxo-3-methylamino-3-phosphonyl-7-oxo-1-aza-2-phospha-cycloheptane was obtained as a monohydrate with a molecular weight of 305 (calc. 304).

Analysis: Calculated: 27.64%, C; 5.96%, H; 9.21%, N; 20.37%, P. Found: 27.63%, C; 5.83%, H; 8.79%, N; 20.25%, P.

In the IR-spectrum of the compound the $\nu$ CO band was at 1625 cm$^{-1}$. After vigorous drying, the compound was obtained in anhydrous form with a molecular weight of 285 (calc. 286). M.P. 274° C with decomposition.

EXAMPLE 8

Sequestration of calcium

In the investigation of the sequestration of calcium, a modified Hampshire test was employed and worked as follows:

1 gm of the sequestering agent was dissolved in 50 ml of $H_2O$, adjusted with NaOH to a pH of 11. 50 ml of a Ca$^{++}$ solution (1470 mg of $CaCl_2.2H_2O/1$) were mixed with 100 ml of a sodium carbonate solution (7.15 gm $NaCO_3.10H_2O/l$.). Then the solution of the sequestering agent was added in drops from a burette until the calcium carbonate precipitate was redissolved. The values formed have been reported in Table I. For the sake of simplicity, only the value for n and the various substituents for R according to Formula I are indicated in the left column of the Table.

TABLE I

R—N—P(=O)—OH, NHR, O=C, C(=O)—OH, (CH$_2$)$_n$—P—OH, OH

R = alkyl having from 1 to 6 carbon atoms
n = 1 to 4

| Compound | | Consumption of Sequestering Agent Solution (ml) | mg CaCO$_3$ Sequestered per gm of Compound |
|---|---|---|---|
| n | R | | |
| 1 | H | 2.6 | 1040 |
| 2 | H | 2.6 | 1040 |
| 2 | CH$_3$ | 3.0 | 840 |
| 2 | C$_2$H$_5$ | 2.25 | 1110 |
| 3 | H | 3.1 | 810 |
| 3 | CH$_3$ | 3.8 | 660 |

Practically identical results were obtained if, instead of the acids, the corresponding sodium, potassium or ammonium salts were employed.

EXAMPLE 9

Threshold effect

The prevention of the precipitation of poorly soluble calcium compounds by substoichiometric amounts of a sequestering agent was determined at 60° and 95° C as follows:

25 ml of 80° dH (German hardness) water (corresponding to 800 mg CaO/l.) were mixed with a 10 ml of a solution of the sequestering agent (concentration: 300 mg/l.). After dilution with distilled water to 70 ml, 25 ml of a sodium carbonate solution containing 4 gm/l. were added and the solution was brought to 100 ml. After heating for 30 minutes at the indicated temperature, any precipitate formed was separated. The sequestering agent was removed from a measured amount of the clear filtrate by means of an anion exchange resin. Then the content of the dissolved calcium in this sample was determined by complexometry (according to Scharzenbach). The following Table II shows the portion of dissolved calcium in percent of the total amount of calcium used.

For the explanation of the data in the left column of the Table, see Example 8.

TABLE II

| Substance | | Temp. °C | CaO in Solution | CaO precipitated |
|---|---|---|---|---|
| n | R | | | |
| 1 | H | 60 | 76.1 | 23.9 |
| | | 95 | 87.7 | 12.3 |
| 2 | H | 60 | 99.6 | 0.4 |
| | | 95 | 99.5 | 0.5 |
| 3 | H | 60 | 99.6 | 0.4 |
| | | 95 | 99.5 | 0.5 |

Practically identical results are obtained if, instead of the acids, the corresponding sodium, potassium or ammonium salts were employed.

EXAMPLE 10

Delay of setting in gypsum

Gypsum materials in the form of plaster, plaster of Paris, or in mixture with aggregates, like limestone, sand, perlite or cellulose, set relatively fast, so that rapid processing must take place. A delay of the setting time can be achieved with the addition of the above-described phosphonic acids, and the processing of the gypsum materials can thus be considerably facilitated.

In the following tests, each of the various phosphonic acids of the invention was added to the water before the gypsum was mixed. However, water-soluble salts of the phosphonic acids, particularly the lithium, sodium, potassium and ammonium salts can also be mixed instead with the gypsum or added shortly after the mixing of the gypsum material together with the water. Specifically the following setting values were found and reported in Table III, using in each test 20.0 gm of gypsum and 9 ml of $H_2O$. The setting time is the time interval in which the gypsum was spreadable and easy to handle.

For the explanation of the data in the left column of Table III, see Example 8.

TABLE III

| Substance | | Amount | Setting Time |
|---|---|---|---|
| n | R | (mg) | (min.) |
| — | — | — | 15 |
| 1 | H | 45 | 50 |
| 2 | H | 45 | 210 |
| 2 | $CH_3$ | 45 | 100 |
| 2 | $C_2H_5$ | 45 | 120 |
| 2 | $C_3H_9$ | 45 | 120 |
| 3 | H | 45 | 120 |
| 3 | $CH_3$ | 45 | 100 |

Comparable results are obtained by using the corresponding magnesium and zinc salts.

EXAMPLE 11

Pharmaceutical application a. Toxicity

The new phosphonic acids are characterized by a very low acute toxicity. The following $LD_{50}$ values of Table IV were found in mice. For the explanation of the data in the left column of Table IV, see Example 8.

TABLE IV

| Substance | | $LD_{50}$ Value |
|---|---|---|
| n | R | gm/kg |
| 2 | H | 3.2 |
| 3 | H | 10.0 | b. Calcium phosphate dissolution in vitro

Essential tests for the effectiveness of the compounds in physiological systems are in vitro tests for the dissolving of freshly precipitated $CaHPO_4$, as well as preventing the precipitation of $NH_4MgPO_4$ at a pH of 7.4. The "$CaHPO_4$ test" was carried out as follows.

By combining 25 ml of a phosphate solution (1.38 gm of $NaH_2PO_4.H_2O$/liter, standardized to a pH of 7.4) and 25 ml of a calcium solution (1.45 gm of $CaCl_2.2H_2O$/liter, standardized to a pH of 7.4), a precipitate of $CaHPO_4$ was produced. Thereafter, so much of a solution of the sequestering agent (at a concentration of 10 mg/ml) was added from a burette that a clear solution was obtained after standing for 1 hour.

The results are compiled in the following Table V. The explanation of the data in the left column is to be found in Example 8.

TABLE V

Dissolution of $CaHPO_4$ Precipitation

| Substance | | Consumption Sequestering Agent Solution | mg $CaHPO_4$ dissolved |
|---|---|---|---|
| n | R | (ml) | gm Sequestering Agent |
| 1 | H | 8.0 | 420 |
| 2 | H | 6.0 | 570 |
| 2 | $CH_3$ | 4.0 | 850 |
| 3 | H | 2.5 | 1350 |
| 3 | $CH_3$ | 5.0 | 680 | c. Inhibition of Precipitation of $NH_4MgPO_4$ in vitro

Since the precipitation of $NH_4MgPO_4$ is occasionally the cause of the formation of urinary calculus, the inhibition of the precipitation of $NH_4MgPO_4$ was also tested in aqueous solutions at pH 7.4. The test was carried out as follows.

A fixed amount of the phosphonic acid was weighed into a beaker and dissolved with 25 ml of a phosphate solution (13.799 gm of $NaH_2PO_4.H_2O$/liter) as well as with 40 ml of distilled water, and standardized with NaOH to a pH of 7.4. After adding 25 ml of a $Mg^{++}$ and $NH_4^+$ solution (20.333 gm of $MgCl_2.6H_2O$ and 5.349 gm of $NH_4Cl$/liter, standardized to a pH of 7.4), the solution was brought up with distilled $H_2O$ to 100 ml. Then the sample was covered and evaluated after 72 hours for amount and appearance of the precipitate. Table VI gives the results of the test. The explanation of the data in the left column is to be found in Example 8.

TABLE VI

Inhibition of $NH_4MgPO_4$ Precipitation

| Substance | | Amount | |
|---|---|---|---|
| n | R | (mg) | Precipitation after 72 hours |
| — | — | — | Clear $NH_4MgPO_4$ crystals, normal crystal form |
| 2 | H | 61 | Few $NH_4MgPO_4$ crystals, some cloudiness |
| | | 122 | No $NH_4MgPO_4$ crystals, great cloudiness |
| 2 | $CH_3$ | 145 | Very few $NH_4MgPO_4$ crystals, no cloudiness |
| | | 217.5 | No $NH_4MgPO_4$ crystals, no cloudiness |
| 3 | H | 68.5 | Fewer $NH_4MgPO_4$ crystals, but great cloudiness |
| 3 | $CH_3$ | 72 | Few $NH_4MgPO_4$ crystals, no cloudiness |
| | | 144 | No $NH_4MgPO_4$ crystals, no cloudiness | d. Apatite crystallization delay test in vitro

Supersaturated solutions of $Ca^{++}$ and $HPO_4^{--}$ ions are relatively stable, but crystallize after the addition of an apatite nuclei according to the reaction

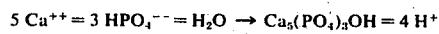

$$5\, Ca^{++} + 3\, HPO_4^{--} + H_2O \rightarrow Ca_5(PO_4)_3OH + 4\, H^+$$

with the release of protons. The reaction can, therefore, be readily observed by titration with a base at a constant pH.

400 ml of 0.0008 molar $KH_2PO_4$ solution were mixed with 45 ml of a 0.012 molar $CaCl_2$ solution, and the clear solution was standardized with KOH to a pH of 7.4, after being brought to a temperature of 35°C. After 30 minutes during which time the pH did not change, a suspension of 100 mg hydroxyl apatite in 50 ml of $H_2O$ was added. The crystallization set in immediately and was followed by "pH-Stat" titration with 0.05 N KOH.

If a small amount (2 mg) of one of the cyclic aminophosphonic acids of the invention was added to the solution before the apatite was added, the crystallization was greatly delayed.

Table VII gives the values of the delay in crystallization. For simplicity's sake, only the value for n and the various substituents for R according to Formula I in Example 8 are indicated in the left column of the Table.

TABLE VII

| Substance | | Delay of crystallization in % after | |
|---|---|---|---|
| n | R | 4 Hours | 8 Hours |
| 2 | $CH_3$ | 84 | 76 |
| 3 | H | 96 | 96 | e. Prevention of hardening of the aorta in rats

The effectiveness of the cyclic aminophosphonic acids of the present invention in preventing abnormal calcium deposits in vivo in rats can be demonstrated as follows.

This test was based on the observation that high doses of vitamin $D_3$ cause a considerable hardening of the aorta in rats. 30 Female rats weighing 150 to 200 gm each were divided into three groups of 10 animals each. They received during the test period a normal diet and tap water ad libitum. One group of 10 animals (control) received no further treatment. Another group of the animals received from the 3rd to the 7th day, 75,000 units of vitamin $D_3$ daily through a stomach sound. The third group likewise received from the 3rd to the 7th day, 75,000 units of vitamin $D_3$ daily through a stomach sound and, in addition, likewise orally, 10 mg per kg of one of the cyclic aminophosphonic acids from the 1st to the 10th day. After 10 days the animals were sacrificed and their aortas prepared and dried for 12 hours at 105°C. After determination of the dry weight, the aortas were ashed; the residue was dissolved, and the calcium was determined by flame photometry. The treatment with cyclic aminophosphonic acid reduced the vitamin $D_3$ induced hardening of the aortas of rats considerably.

For the production of a pharmaceutical preparation in the form of a capsule, the known methods of preparation are followed to prepare capsules having a content per capsule as follows:

| | |
|---|---|
| Cyclic aminophosphonic acid derivative of Formula I | 100 mg |
| Starch | 20 mg |
| Sodium laurylsulfate | 1 mg |

For the preparation of a tablet, the following recipe was utilized per tablet:

| | |
|---|---|
| Cyclic aminophosphonic acid derivative of Formula I | 50 mg |
| Lactose | 100 mg |
| Starch | 35 mg |
| Magnesium stearate | 2 mg |

Any of the cyclic aminophosphonic acid derivatives of Formula I can be employed in the above compositions. It is preferable, however, to employ the acids partially neutralized with sodium, potassium or ammonium.

EXAMPLE 12

Cosmetic Preparations

The following recipes are suitable as a basic formula for tooth pastes:

| | | Parts by Weight |
|---|---|---|
| (a) | Glycerin | 60.0 |
| | Water | 13.5 |
| | Sodium carboxymethyl-cellulose | 0.6 |
| | Sodium xero gel | 20.0 |
| | Sodium laurylsulfate | 2.0 |
| | Essential oils | 1.0 |
| | Sweetening agent | 0.4 |
| | Cyclic aminophosphonic acid | 2.5 |
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silica | 1.5 |
| | Essential oils | 1.5 |
| | Sweetening agent | 0.5 |

| | Parts by Weight |
|---|---|
| Cyclic aminophosphonic acid | 2.0 |

Suitable as a basic formulation for mouthwashes is the following recipe:

| | Parts by Weight |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| Cyclic aminophosphonic acid | 2.5 |

Any one of the compounds described in Examples 1 to 7 were used as the cyclic aminophosphonic acid.

By regular use of the mouthwashes and/or toothpastes containing the above-mentioned cyclic aminophosphonic acids, the formation of tartar could be considerably reduced. The formation of hard compact plaque on the teeth was to a great extent prevented.

The preceding specific embodiments are illustrative of the practice of the invention. It is to be understood, however, that other expedients known to those skilled in the art or discussed herein may be employed without departing from the spirit of the invention or the scope of the appended claims.

We claim:

1. A method for alleviating conditions caused by the abnormal deposition or dissolution of difficultly soluble calcium salts in the body of warm-blooded animals having said condition which consists of administering to said warm-blooded animals a safe but effective amount for said treatment of from 0.05 to 500 mg per kg of the body weight of a pharmacologically acceptable cyclic aminophosphonic acid derivative selected from the group consisting of (1) a compound of the formula

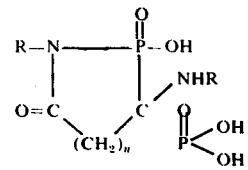

wherein R is a member selected from the group consisting of hydrogen and alkyl having from 1 to 6 carbon atoms and $n$ is an integer from 1 to 3, and (2) a nontoxic pharmacologically acceptable water-soluble salt thereof.

2. The method of claim 1 wherein $n$ is 1 and R is hydrogen.

3. The method of claim 1 wherein $n$ is 2 and R is hydrogen.

4. The method of claim 1 wherein $n$ is 2 and R is methyl.

5. The method of claim 1 wherein $n$ is 2 and R is ethyl.

6. The method of claim 1 wherein $n$ is 2 and R is n-butyl.

7. The method of claim 1 wherein $n$ is 3 and R is hydrogen.

8. The method of claim 1 wherein $n$ is 3 and R is methyl.

9. The method of claim 1 wherein said water-soluble salt is selected from the group consisting of alkali metal and ammonium salts.

* * * * *